(12) United States Patent
Sokel et al.

(10) Patent No.: US 8,756,789 B2
(45) Date of Patent: Jun. 24, 2014

(54) METHOD OF MANUFACTURING A CATHETER ASSEMBLY

(75) Inventors: Justin W. Sokel, Flagstaff, AZ (US); Stanislaw L Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 210 days.

(21) Appl. No.: 13/297,036

(22) Filed: Nov. 15, 2011

(65) Prior Publication Data

US 2012/0143302 A1 Jun. 7, 2012

Related U.S. Application Data

(60) Provisional application No. 61/414,270, filed on Nov. 16, 2010.

(51) Int. Cl.
*B21D 39/00* (2006.01)
*A61M 25/16* (2006.01)
*A61M 25/00* (2006.01)

(52) U.S. Cl.
CPC ........ *A61M 25/0067* (2013.01); *A61M 25/0069* (2013.01)
USPC ................... 29/505; 29/508; 29/520; 604/523

(58) Field of Classification Search
CPC ................... A61M 25/0054; A61M 25/0067; A61M 25/0069
USPC ............. 29/505, 508, 520; 604/523, 915, 921
See application file for complete search history.

(56) References Cited

U.S. PATENT DOCUMENTS

| | | | | |
|---|---|---|---|---|
| 2003/0233037 | A1* | 12/2003 | Bencini | 600/374 |
| 2008/0132989 | A1* | 6/2008 | Snow et al. | 623/1.12 |
| 2010/0152574 | A1* | 6/2010 | Erdman et al. | 600/424 |

FOREIGN PATENT DOCUMENTS

| | | |
|---|---|---|
| GB | 1332062 A * | 10/1973 |
| WO | 94/15549 | 7/1994 |
| WO | 2009/134801 | 11/2009 |

* cited by examiner

*Primary Examiner* — Jermie Cozart
(74) *Attorney, Agent, or Firm* — Gilbert R. Gabo

(57) ABSTRACT

A catheter assembly includes a catheter having a proximal end and a distal end; an expandable device releasably attached to the catheter near the distal end; a generally tubular constraining sleeve extending around and compressing the device to an outer peripheral dimension suitable for endoluminal delivery; a tip fixedly secured to the distal end of the catheter; and a bridge member disposed between the tip and the expandable device so as to fill a gap therebetween as the catheter assembly is bent during endoluminal delivery of the expandable device to a treatment site.

5 Claims, 7 Drawing Sheets

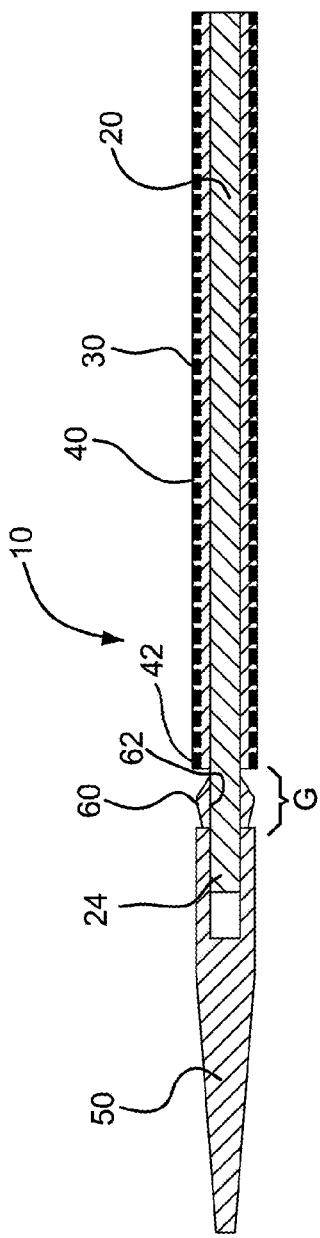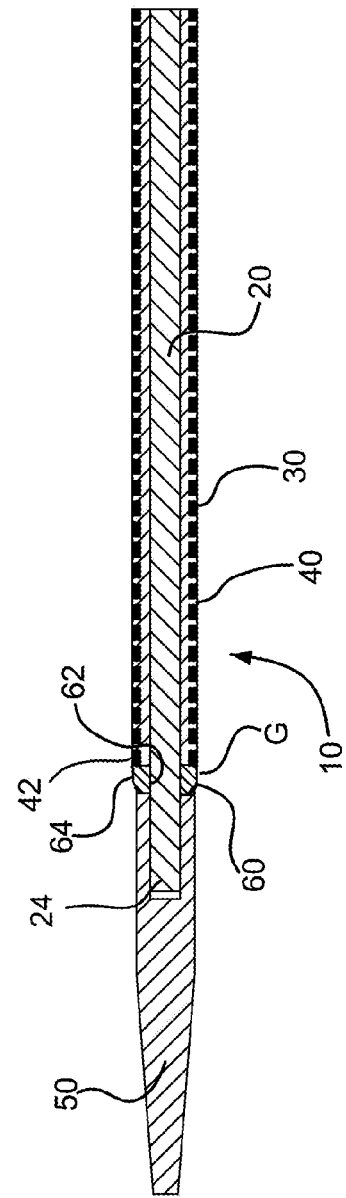

METHOD OF MANUFACTURING A CATHETER ASSEMBLY

CROSS REFERENCE TO RELATED APPLICATIONS

This application is a non-provisional of, and claims priority to, U.S. Provisional Patent Application No. 61/414,270, entitled "Medical Apparatus and Method of Making The Same," filed Nov. 16, 2010, the content of which is hereby incorporated by reference in its entirety.

BACKGROUND

1. Field

The present disclosure relates to catheter-based systems used to deliver medical devices.

2. Discussion of the Related Art

Various medical devices require catheter based delivery systems. Such medical devices include implantable, diagnostic and therapeutic devices. Common implantable, endovascular devices can include stents, stent grafts, filters, occluders, sensors and other devices. Endovascular devices are commonly advanced through the native vasculature to a treatment site by the use of a flexible catheter. When properly positioned at the treatment site the device (in the case of a stent) can be expanded to appose the vasculature. The device can then be released from the catheter allowing the catheter to be withdrawn from the vasculature. It is desirable to pre-compact endovascular devices into small delivery profiles in order to minimize vascular trauma and enhance maneuverability through torturous anatomies. A highly compacted device is often relatively stiff and is therefore difficult to bend into a small radius. A soft, flexible "olive" or tip is commonly positioned distal to the compacted device at the leading end of the delivery catheter, again to minimize vascular trauma and to enhance the positioning accuracy. As the device is advanced through a curved vessel, the junction between the relatively stiff compacted device and the soft flexible tip can "open up" presenting a gap.

It remains desirable to have a device delivery system incorporating a means to cover any potential gap between the compacted device and a leading catheter tip.

BRIEF DESCRIPTION OF THE DRAWINGS

In the following drawings:

FIG. 1 is a cross-sectional view of a catheter assembly in accordance with various embodiments with a bridging member shown in an uncompressed state between a distal tip and device of the catheter assembly.

FIG. 2 is a cross-sectional view of the catheter assembly in FIG. 1 with the bridging member shown in a compressed state between the distal tip and catheter assembly.

DETAILED DESCRIPTION

Figure 4:
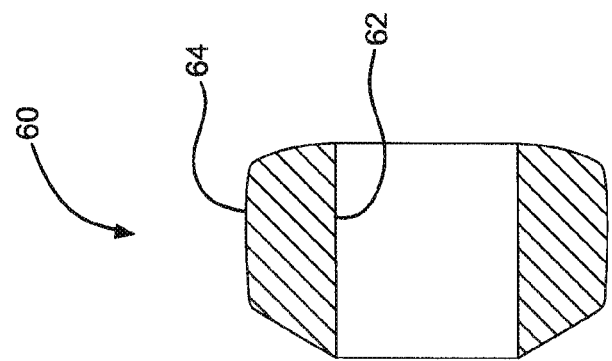
FIG. 4 is a cross-sectional view of the bridging member of FIG. 1 in the compressed state.

Referring to FIGS. 1 and 2, a catheter assembly in accordance with various embodiments is shown and generally indicated at 10. The catheter assembly 10 includes a catheter 20, an expandable device 30, a generally tubular restraining member or "constraining sleeve" 40 and a tip 50. The catheter 20 extends longitudinally between opposite proximal 22 and distal 24 ends. The expandable device 30 is releasably attached to the catheter 20 near the distal end 24 of the catheter 20. The constraining sleeve 40 is disposed around and compresses the device 30 to an outer peripheral dimension suitable for endoluminal delivery to a treatment site in a patient. The constraining sleeve 40 has a distal end 42 that faces the distal end 24 of the catheter 20. Examples of restraining members or constraining sleeves for releasably maintaining expandable devices in a collapsed state for endoluminal delivery can be found in U.S. Pat. No. 6,352,561 to Leopold et al, the content of which is incorporated herein by reference in its entirety. Described in greater detail below, the catheter assembly 10 further includes a bridge member 60 disposed generally between the tip 50 and the expandable device 30 to fill a gap therebetween.

Figure 3:
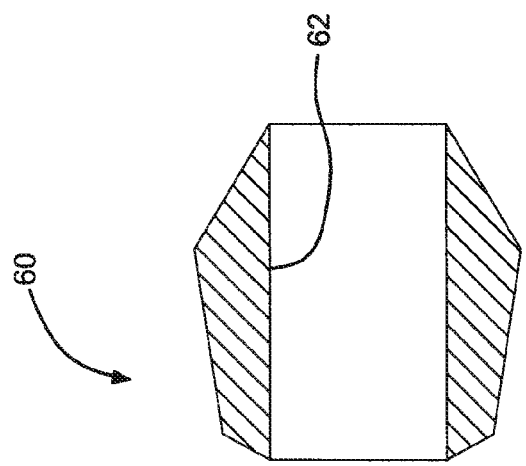
FIG. 3 is a cross-sectional view of the bridging member of FIG. 1 in the uncompressed state.

In FIG. 1, the bridge member 60 is shown positioned along a gap "G" between the tip 50 and the device 30. The bridge member 60, as shown, is not yet fully assembled to the catheter assembly 10 and is in an uncompressed state (also illustrated in FIG. 3). During assembly of the catheter assembly 10, the device 30 is positioned along the catheter 20 and compressed or crushed onto the catheter by the constraining sleeve 40 so as to have an outer peripheral dimension suitable for endoluminal delivery. The bridge member 60 includes a bore 62 through which the distal end 24 of the catheter 20 is inserted. The tip 50 is then placed onto the distal end 24 of the catheter 20. The tip 50 is pressed axially toward the device 30, and the bridge member 60 is compressed generally axially between the tip 50 and the device 30, as shown in FIG. 2. The tip 50 is fixedly secured to the distal end 24 of the catheter 20 and thereby retains the bridge member 60 in the compressed state (also illustrated in FIG. 4). The tip 50 may be fixedly secured to the distal end 24 of the catheter 20 by a variety of fixing methods, such as by using UV-cured adhesives, ultrasonic welding, reflow bonding, press fits, or other joining methods known in the art.

In one embodiment, the bridge member 60 is compressed elastically between the tip 50 and the device 30 so that as the catheter assembly 10 is bent, such as during endoluminal delivery, the bridge member 60 continues to fill the gap between the tip 5 and the device 30 as well as maintain a generally continuous, transitional surface 64 therebetween. More specifically, as the catheter assembly 10 is bent, the bridge member 60 is further compressed along an inner curve of the bend and at the same time allowed to expand or relax along an outer curve of the bend.

Figure 5:
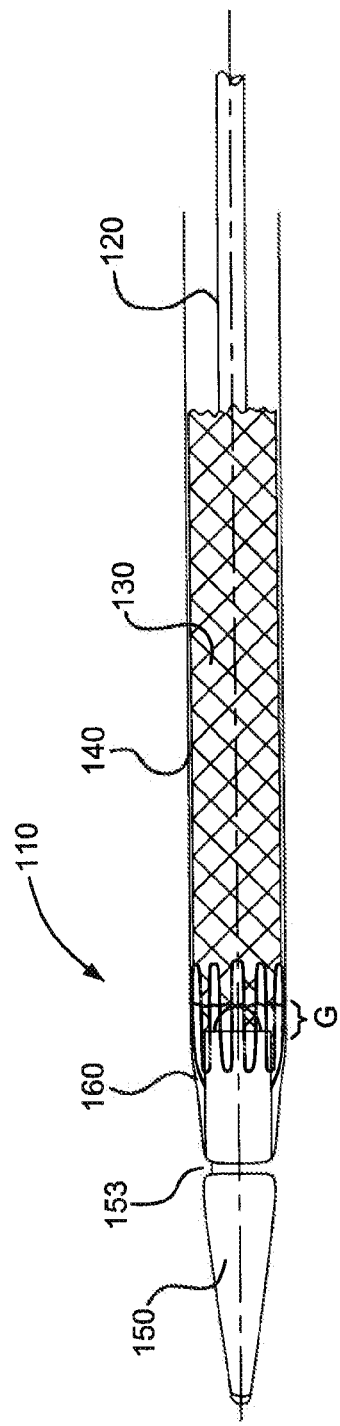
FIG. 5 is a side view of a catheter assembly in accordance with various embodiments.
Figure 6:
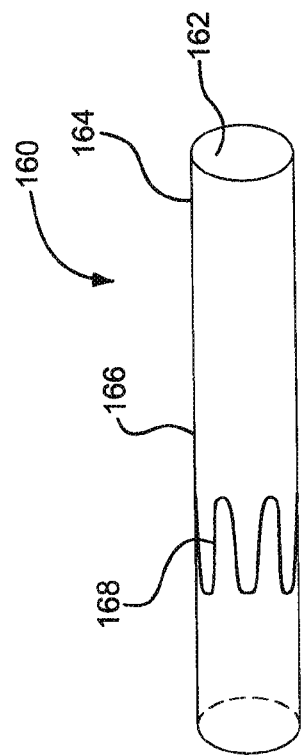
FIG. 6 is a perspective view of a bridging member of the catheter assembly shown in FIG. 5.

In FIGS. 5 and 6, an alternative embodiment of a catheter assembly is shown and generally indicated at 110. The catheter assembly 110 of this embodiment includes a generally tubular bridge member 160 having a lumen or bore 162 defined by a generally cylindrical side wall 166. The side wall 166 may be constructed of ePTFE, or other materials such as FEP, PET, or other medical grade flexible polymers. The bridge member 160 also includes a wire frame 168. The wire frame 168 may be formed from Nitinol. Alternatively, the wire frame may be formed from L605, 304V, MP35N, 316L, or any other medical grade allow. The wire frame 168 may have a generally sinusoidal shape extending peripherally about the side wall 166. The wire frame may also be formed into other shapes depending on the specific treatment needs.

Referring specifically to FIG. 5, the tip 150 may include a circumferential groove 153 onto which the bridge member 160 can be coupled or secured to the tip 150. For example, a releasable shrink tube may be applied about the bridge member 160 along the groove 153 to secure the bridge member 160 to the tip 150.

Figure 7:
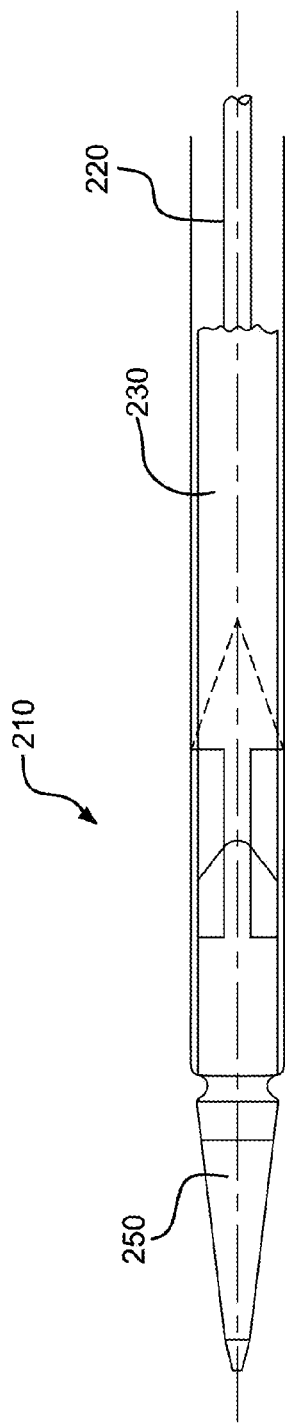
FIG. 7 is side view of a catheter assembly according to various embodiments.
Figure 8:
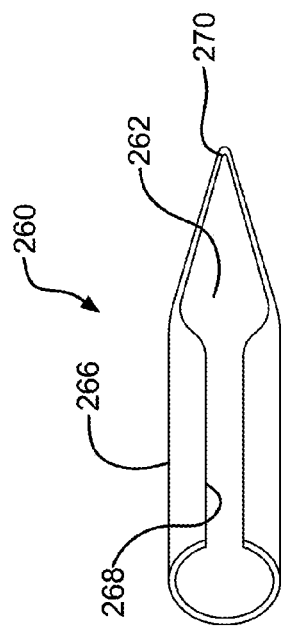
FIG. 8 is a perspective view of the a bridging member of the catheter assembly shown in FIG. 7.

In FIGS. 7 and 8, another alternative embodiment of a catheter assembly is shown and generally indicated at 210. The catheter assembly 210 of this embodiment includes a generally cylindrical or tube shaped bridge member 260 having an a longitudinally extending slot 268. The bridge member 260 is formed from a metal or metal alloy, such as Nitinol, L605, 304V, MP35N, 316L, or any other medical grade allow. In assembly, the slot 268 allows the bridge member 260 to be expanded radially and elastically to allow insertion of a proximal end of the tip 250 through the bridge member lumen 262. The bridge member 260 is then allowed to return toward its untensioned state and contract toward its untensioned dimension, thereby coupling the bridge member 260 to the tip 250. As in the previous embodiments, the bridge member 260 fills the gap between the tip 250 and the device 230, even as the catheter assembly 210 is bent during endoluminal delivery. The bridge member 260 includes a generally pointed or narrowing proximal tip 270 that facilitates retraction of the catheter assembly 210 through a sheath (not shown).

Figure 9:
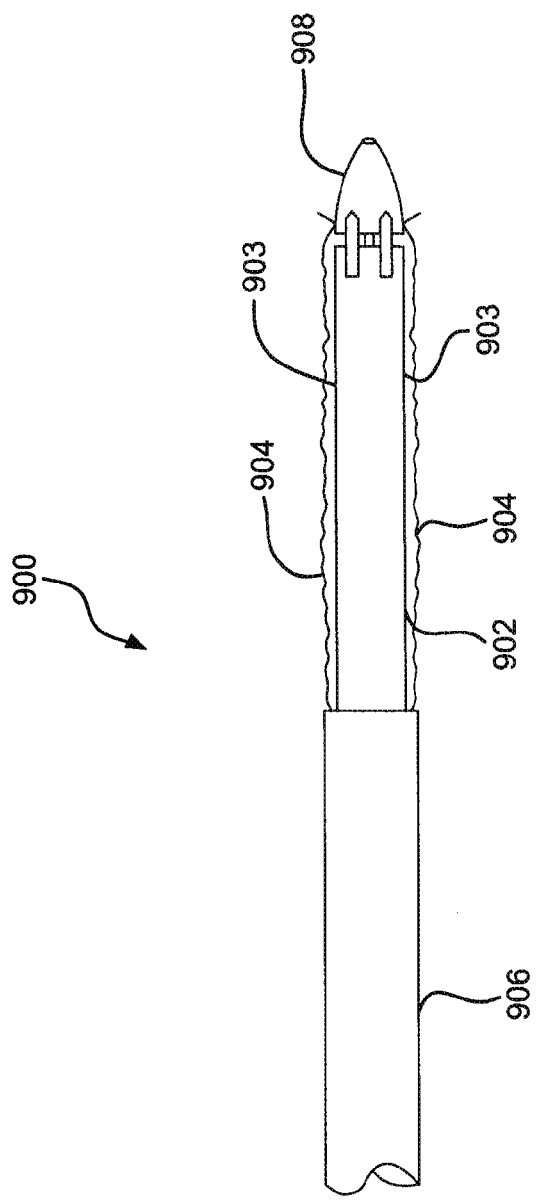
FIG. 9 is a perspective view of a bridging member in accordance with various embodiments.
Figure 10:
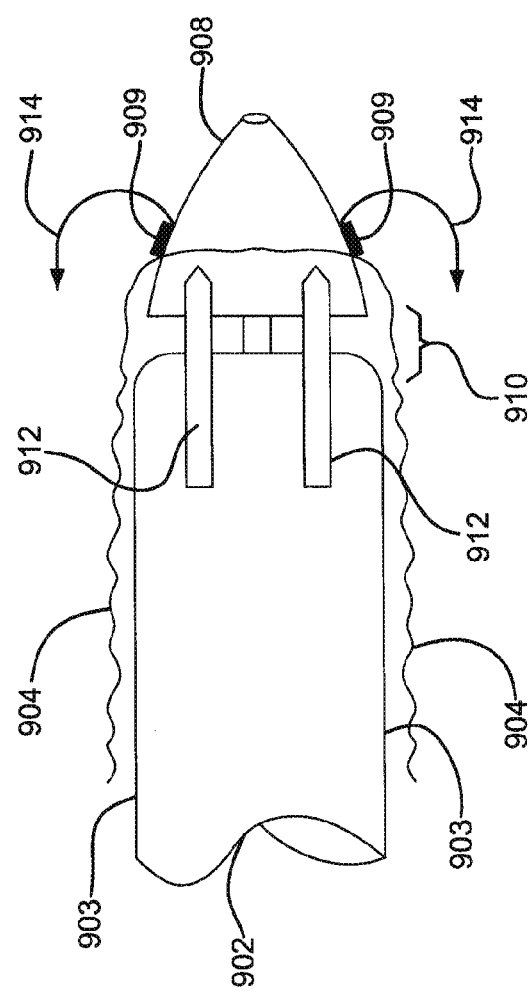
FIG. 10 is an enlarged perspective view of the bridging member in FIG. 9.
Figure 11:
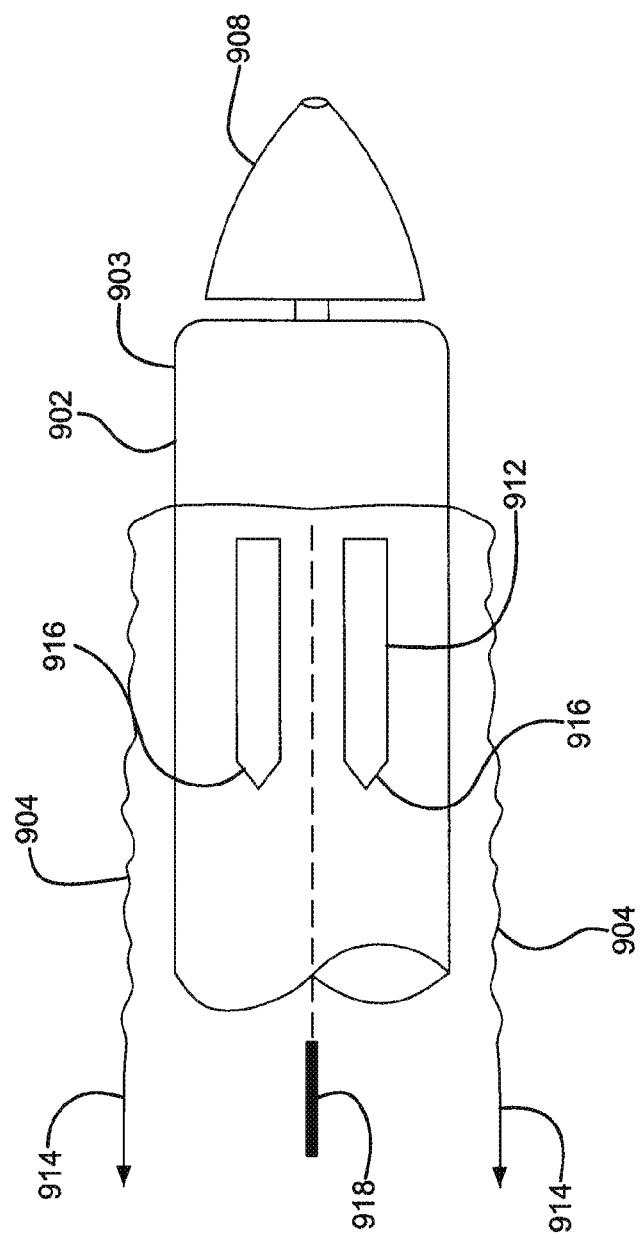
FIG. 11 is an enlarged perspective view of a catheter assembly incorporating the bridging member in FIG. 9 and a protective outer sleeve cutting blade.

A catheter assembly in accordance with various embodiments is shown illustratively in FIGS. 9-11. Referring to FIG. 9, a partial view of a proximal end of a delivery system 900 is shown for positioning a compacted medical device 902. The medical device 902 is constrained by a tubular sleeve 903 and is adjacent to a delivery catheter 906. Covering the compacted device 902 and the tubular sleeve 903 is a protective sleeve 904. The protective sleeve 904 provides a smooth outer surface to the delivery system 900, enhancing device positionability and compatibility with a distal hemostatic valve (not shown). Also shown is a catheter proximal tip 908. FIG. 10 is an enlarged view of the proximal end of the delivery system of FIG. 9. Shown is a compacted medical device 902, tubular constraining sleeve 903, a proximal catheter tip 908 and a protective outer sleeve 904. The protective outer sleeve 904 is shown releasably attached 909 to the proximal catheter tip 908. A gap 910 is shown between the proximal catheter tip 908 and the compacted medical device 902. A series of semi-rigid bridge straps 912 are shown spanning the gap 910. The bridge straps can be embedded into the protective outer sleeve 904. The bridge straps 912 provide a smooth transition between the proximal catheter tip 908 and the compacted medical device 902. The bridge straps 912 also allow the junction between the proximal catheter tip 908 and the compacted medical device 902 to flex when the delivery system 900 traverses torturous anatomy. Prior to device deployment, the protective outer sleeve 904 can be withdrawn by everting the sleeve back onto itself. The protective outer sleeve 904 can be everted by applying tension to the sleeve end as shown by direction arrows 914. The tension can be applied by pull lines or other means attached to the proximal end of the protective outer sleeve 904. When adequate tension is applied to the protective outer sleeve 904 the releasable attachment 909 is released allowing the sleeve to evert. The releasable attachment can be an adhesive join, or use other releasable attachment means as commonly known in the art. As further tension 914 is applied, the protective outer sleeve 904 further everts as shown in FIG. 11. The semi-rigid bridge straps 912 (embedded into the protective outer sleeve 904) bend and become reversed as shown in FIG. 11. The semi-rigid bridge straps 912 can optionally incorporate pointed or chamfered leading ends 916. The chamfered leading ends 916 will allow an optional cutting blade 918 to self-align to the gaps between the semi-rigid bridge straps 912 allowing the protective outer sleeve 904 to be longitudinally split. The split protective outer sleeve 904 can be subsequently fully removed from the catheter system. Semi-rigid bridge straps 912 can be fabricated from a variety of metallic or polymeric materials as commonly known in the art.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of manufacturing a catheter assembly including:
   providing a catheter having a distal end and an expandable device fixedly secured thereto;
   providing a bridge member generally coaxial with the catheter and disposed onto an exposed portion of the distal end of the catheter;
   providing a tip generally coaxial with the catheter and disposed onto the exposed portion of the distal end of the catheter;
   axially compressing the bridge member between the expandable device and the tip; and
   fixedly securing the tip to the catheter to retain the bridge member in the compressed state between the expandable device and the tip.

2. The method as set forth in claim 1 including axially compressing the bridge member toward the device so as to outwardly radially tension the expandable device.

3. The method as set forth in claim 1 including compressing the expandable device with an outer constraining sleeve to an outer dimension suitable for endoluminal delivery.

4. The method as set forth in claim 3 including axially compressing the bridge member toward the device to cause outward displacement of the bridge member to a desired outer profile.

5. The method as set forth in claim 3 including axially compressing the bridge member toward the device to cause outward displacement of the bridge member to an outer profile that provides a transition between the tip and the expandable device.

* * * * *